(12) United States Patent
Shah et al.

(10) Patent No.: US 6,387,405 B1
(45) Date of Patent: *May 14, 2002

(54) VELVETY HYDROCARBON BASED COSMETIC COMPOSITIONS

(75) Inventors: Amit R. Shah, Commack; Linda Najdek, E. Islip; Jeffrey Ehrenberg, New York; Nicole B. Huggins, Westbury; Aya Shidara, Mineola, all of NY (US); Carl C. Orr, Scotch Plains, NJ (US)

(73) Assignee: E-L Management Corp., New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/032,614

(22) Filed: Feb. 27, 1998

(51) Int. Cl.[7] ................................................. A61K 9/14
(52) U.S. Cl. ........................... 424/486; 424/63; 424/64; 514/844
(58) Field of Search .............................. 424/401, 486, 424/501, 63–64; 514/944, 844

(56) References Cited

U.S. PATENT DOCUMENTS

| | | |
|---|---|---|
| 4,742,142 A | 5/1988 | Shimizu et al. |
| 4,980,167 A | 12/1990 | Harashima et al. |
| 5,266,321 A | 11/1993 | Shukuzaki et al. |
| 5,599,533 A | 2/1997 | Stepniewski et al. |
| 5,919,468 A * | 7/1999 | Bara |
| 5,985,807 A * | 11/1999 | Aubuste et al. |
| 6,027,738 A * | 2/2000 | Stepniewski et al. |

FOREIGN PATENT DOCUMENTS

| | | |
|---|---|---|
| EP | 0 295 886 B1 | 1/1992 |
| EP | 0 790 055 A1 | 8/1997 |
| EP | 850643 | 7/1998 |
| EP | 852945 | 7/1998 |
| FR | 2757379 | 6/1998 |
| JP | 07258028 | 10/1995 |
| WO | WO 98 00105 | 1/1998 |

* cited by examiner

Primary Examiner—Edward J. Webman
(74) Attorney, Agent, or Firm—Dorene M. Price, Esq.; Karen A. Lowney, Esq.

(57) ABSTRACT

The present invention relates to cosmetic compositions for topical application to the skin. The compositions comprise an organopolysiloxane elastomer dispersed in a hydrocarbon vehicle. The present invention also includes a cosmetic composition comprising a silicone gel combined with a compatible cosmetically acceptable carrier where the silicone gel comprises the elastomer dispersed in the vehicle. The compositions of the invention are transfer resistant and produce a unique soft and powdery sensation on the skin due to the combination of the elastomer with the hydrocarbon vehicle.

15 Claims, No Drawings

VELVETY HYDROCARBON BASED COSMETIC COMPOSITIONS

FIELD OF THE INVENTION

The invention relates to cosmetic compositions. More specifically, the invention relates to cosmetic compositions comprising an organopolysiloxane elastomer and a hydrocarbon vehicle which results in a makeup cosmetic product that feels soft and powdery on the skin and is transfer resistant.

BACKGROUND OF THE INVENTION

Consumers desire makeup which they can apply smoothly and easily on their skin. They also want makeup to feel good and stay on their skin after it is applied. However, many makeup formulations that provide different types of appearances on the skin, feel less than desirable on the skin. For example, in order to achieve various "looks" that makeup can have on the skin, the makeup base is formulated with additional solids and fillers. Consequently, these makeup formulations feel greasy or oily, sticky or heavy, or drag or cake on the skin. While the makeup may provide a certain look, overall, the makeup does not feel good on the skin during and after application. To overcome this challenge, it is well known in the art to use silicone in the formula because it improves the feel of the makeup on the skin.

In recent years, there has been a strong trend toward the use of silicone fluids in makeup products. Silicones provide an elegant feel in that the makeup containing them goes onto the skin smoothly, with an excellent slip, and yet does not produce the greasy, heavy feel that non-silicone oils frequently have. Despite the excellent characteristics of silicone oil, especially that of low viscosity silicone oils which give a less sticky fresh feeling, it does not provide a fresh feeling on the skin.

Silicone oils remain attractive because of their tendency to produce a very shiny appearance on the skin. However, for certain types of cosmetic products, and/or for certain types of consumers, a significant amount of shininess is not desired. Therefore, attempts have been made using higher levels of pigment. The problem that frequently occurs is that the makeup is heavy and cakey, and does not feel good on the skin of a majority of consumers.

One type of look, for example, that certain consumers desire from their makeup is what is commonly referred to as a "matte" look. Traditionally, matte makeup has been achieved by the addition of solid powders, such as mica, silica, talc, and the like, to the formulation. In the case of silicone oil-based compositions, however, counteracting the shine produced tends to be more difficult than with more conventional cosmetic oils, thus requiring the addition of even greater amounts of solid fillers. The larger proportion of solids in a formulation, however, results in the heavy, draggy feel on the skin. Therefore, the benefit of the silicone oil is to some extent canceled.

There remains a need for base formulations which can confer a variety of appearances on the skin of the user without feeling draggy and heavy on the skin due to the necessity of using a large percentage of solids or fillers in the formulation. The present invention provides such a method, as well as non-silicone oil based formulations which are transfer resistant on the skin.

SUMMARY OF THE INVENTION

The invention relates to cosmetic compositions for topical application to the skin. Specifically, the composition comprises an organopolysiloxane elastomer dispersed in a hydrocarbon vehicle which produces a powdery feeling on the skin. The present invention also includes a method of producing a cosmetic which comprises adding to a compatible cosmetically acceptable carrier a silicone gel comprising an organopolysiloxane elastomer dispersed in a hydrocarbon vehicle.

It has been unexpectedly discovered that use of a gel base makeup formulation which includes the silicone gel combined with the compatible cosmetically acceptable carrier effectively provides a makeup product that feels velvety when applied on the skin. The resulting cosmetic compositions are also transfer resistant and appear soft, light, and attractive on the skin; the combination of the silicone gel with the compatible cosmetically acceptable carrier improves the feel and slip of makeup products.

DETAILED DESCRIPTION OF THE INVENTION

A cosmetic composition having long-lasting and unique tactile properties is provided in the present invention. The composition comprises an organopolysiloxane elastomer dispersed in a hydrocarbon vehicle. The elastomer dispersed in the hydrocarbon vehicle together form a silicone gel that is in turn, combined with a compatible cosmetically acceptable carrier to produce a cosmetic composition that possesses a characteristic soft and powdery feel on the skin and is also transfer resistant. Therefore, the present invention also includes a cosmetic composition comprising the silicone gel in combination with the compatible cosmetically acceptable carrier.

The term "hydrocarbon vehicle" as used in the present specification and claims is any cosmetically acceptable hydrocarbon oil. The hydrocarbon vehicle can be a volatile or a non-volatile hydrocarbon oil. Suitable volatile oils include straight (i.e., linear) or branched chain volatile hydrocarbon oils having from 1 to 14 carbon atoms, such as decane, dodecane, tridecane, tetradecane, and C8–20 isoparaffins; non-volatile hydrocarbons include but are not limited to isoparaffins, squalane, or petrolatum, or mixtures thereof. The hydrocarbon vehicle is present in an amount of about 5 to about 60 percent by weight of the silicone gel. In a preferred embodiment, the hydrocarbon vehicle is isododecane.

The silicone gel of the present invention is prepared by dispersing in the hydrocarbon vehicle, the organopolysiloxane elastomer. Gels of this type have been previously disclosed for use in water-in-oil emulsion products, for example in U.S. Pat. No. 5,599,533. Silicone gels:

have also been reported in anhydrous non-silicone oil-based products in U.S. Pat. No. 5,266,321. However, they have not previously been dispersed in a hydrocarbon vehicle and combined in makeup products with any compatible carrier, and the ability of such products to provide a soft powdery feel on the skin has not previously been disclosed.

Combining the gels (i.e., the elastomer and the hydrocarbon vehicle) in any compatible carrier yields a cosmetic product that feels soft and powdery on the skin and is transfer resistant. Advantageously, the gels combined with the compatible carrier permit the production of "soft-focus" and matte-finish products without feeling heavy, greasy or oily, or caking or dragging on the skin caused by the addition of solids and fillers. In a preferred embodiment of the present invention, the silicone gel is present in an amount of about 5 to about 60 percent by weight of the composition.

Specifically, the elastomer of the present invention is a reaction product of an organopolysiloxane having an unsaturated group bound to a terminal silicon atom and an organohydrogensiloxane which reaction product is at least partially cross-linked. Cross-links are junctions of polymer strands in a three-dimensional structured network. They are like long-chain branches which are so numerous that a continuous insoluble gel is formed. An elastomer is generally, a chain polymer having a degree of cross-linking sufficient to provide a gel-like substance. Such an elastomer may have a viscosity of about 100,000 to 1,000,000 cps. The elastomer can be cured by mechanisms known in the art such as addition-type or condensation-type.

The organopolysiloxane elastomers of the present invention are hetero-chain polymers. Preferred organopolysiloxane are ones which are at least partially cross-linked addition reaction products, i.e., hydrosilation products, or addition polymerization products, of an organopolysiloxane having unsaturated groups, such as vinyl or allyl, preferably bonded to at least one terminal silicon atom, and another silicone compound capable of participation in the addition reaction, such as an organohydrogenpolysiloxane. Suitable organopolysiloxane elastomers having a partial three-dimensional cross-linked structure, are described, for example, in U.S. Pat. No. 5,266,321, the contents of which are incorporated herein by reference. However, other suitable elastomer materials are disclosed in, for example, U.S. Pat. Nos. 4,980,167, 4,742,142, EP 790055, and EP 295886.

The chosen elastomer is dispersed in the hydrocarbon vehicle by known homogenization techniques. The elastomer dispersed in the vehicle provides a soft, stable viscous gel, or gel-like material. Alternatively, the gel can be purchased premade, with the elastomer already dispersed in the vehicle. In a preferred embodiment of the present invention, the silicone gel is a premade product that is offered commercially under the name Gransil (e.g., Gransil IDS) from Grant Industries, Inc., Elmwood Park, N.J., or it may be obtained from other commercial sources. A mixture of these commercial products may also be used. The amounts of elastomer and vehicle may vary, depending on the desired viscosity, but generally they should be in the range of about 35 to about 65 percent for the elastomer and the vehicle, respectively. In a preferred embodiment, they are in about a 50:50 ratio. The gel, in the preferred embodiment, is polysilicone-11, which is also a commercially available product.

By "compatible carrier" in the present specification and claims is meant any cosmetically acceptable oil which is compatible with the silicone gel. The carrier comprises, in the composition as a whole, preferably at least about 0.5 to about 60 percent by weight. The compatible carrier is one that does not interfere with the soft powdery feel of the silicone gel comprising the organopolysiloxane elastomer in combination with the hydrocarbon vehicle. In addition, the compatible carrier can be the same as or different than the hydrocarbon vehicle.

A preferred compatible carrier can be any cosmetically acceptable hydrocarbon oil in which the elastomer is dispersible. The hydrocarbon oil can be volatile or non-volatile. The volatile hydrocarbon oil can be a linear or branched chain hydrocarbon having at least about 1 to about 14 carbon atoms. In a preferred embodiment, the hydrocarbon oil is volatile and more preferably, it is isododecane. The carrier can also be any cosmetically acceptable silicone oil. The silicone oil can be any volatile or non-volatile silicone, or any combination thereof. Suitable volatile oils include cyclic and linear silicones, such as hexamethylcyclotrisiloxane, octamethylcyclotetrasiloxane, and decamethylcyclopentasiloxane or volatile linear dimethylpolysiloxanes; suitable non-volatile silicones include but are not limited to dimethicone, dimethiconol, phenyl trimethicone, simethicone, organomodified versions of any of these, or mixtures thereof. The silicone oil may be present in an amount of at least about 0.5 to about 10 percent when combined with hydrocarbon oil.

In addition to the primary components of the compatible carrier, other oil or oil-like emollients may be employed, in which case they may be present in an amount of about 1 to about 10 percent by weight of the composition. Examples of suitable oils or oil-like emollients, as well as other optional ingredients, can be found in the International Cosmetic Ingredient Handbook, CTFA, 1996, the contents of which are incorporated herein by reference. Useful materials include, but are not limited to, castor oil, coconut oil, corn oil, jojoba oil, cottonseed oil, soybean oil, walnut oil, wheat germ oil, sunflower seed oil, palm kernel oil, calendula oil, C10-18 triglycerides, lanolin and lanolin derivatives, illipe butter, shea butter; esters having the formula RCO—OR' wherein RCO represents a carboxylic acid radical and OR' represents an alcohol residue, such as isodecyl neopentanoate, tridecyl octanoate, cetyl palmitate, cetyl octanoate, cetyl stearate, cetyl myristate, isopropyl palmitate, isopropyl myristate, polyglyceryl-2-isostearate, neopentyl glycol distearate, isodecyl oleate, decyl isostearate, diisopropyl sebacate, PEG-4 diheptanoate, dioctyl malate, and isohexyl neopentanoate; and fatty alcohols, such as lanolin alcohol or oleyl alcohol.

In a preferred embodiment of the present invention, the benefit of combining the gel in a hydrocarbon oil carrier is obtained in any type of anhydrous composition. The compositions of the present invention can be used in any type of makeup or, skin or sun care product. Typical examples include foundations, eyeshadows, eyeliners, mascaras, blushes, powders, lipsticks, lipglosses, lip paints, oil control skin mattifiers, and sunscreen lotions. Alternately, however, the gel may form part of the oil phase of a water-in-oil or oil-in-water emulsion. In formulating the product, the silicone gel is simply added to a compatible cosmetically acceptable carrier. As an alternative, the elastomer component of the gel can be added directly to the cosmetically acceptable carrier, if the carrier contains a hydrocarbon oil.

Although the makeup compositions prepared in this way possess a significant level of transfer resistance, this property can be further improved by the addition of a film forming agent. Accordingly, another optional component of the formulation is one or more film forming agents. The use of a film former improves the wear of the composition, and can confer transfer-resistance to the makeup product. Examples of useful film forming agents include natural waxes, polymers such as polyethylene polymers and copolymers of polyvinylpyrrolidone ("PVP"), dimethicone gum, and resins, such as shellac, polyterpenes, and various silicone resins. A particularly preferred film former is trimethylsiloxysilicate and may be present in an amount of from about 0.1 to about 20 percent by weight of the composition.

It may also be desirable to incorporate one or more waxes in the composition, particularly if the product is a lipstick or other makeup products in the form of a stick. The term "wax" will be understood to encompass not only waxes in the traditional sense, i.e., those plant, animal or mineral waxes containing primarily esters of higher fatty acids and alcohols, free higher acids and alcohols, and saturated hydrocarbons, but also synthetic resinous products having a wax-like, i.e., hard, brittle, relatively non-greasy texture at room temperature, such as silicone waxes. Examples of suitable waxes include, but are not limited to, carnauba wax, candelilla wax, beeswax, microcrystalline wax, polyethylene, japan wax, synthetic wax, shellac wax, spermaceti, lanolin wax, ozokerite, bran wax, ceresin wax, bayberry wax, paraffin, rice wax, mink wax, montan wax, ouricoury wax, jojoba wax, and the like.

Additional preferred components of the cosmetic compositions of the invention include one or more pigments. Any cosmetically acceptable pigment, either organic, inorganic, or combinations thereof, can be used in the makeup compositions of the invention. Examples of useful inorganic pigments include iron oxides (yellow, red, brown or black), ultramarines, chromium hydroxide green, chromium oxide, titanium dioxide (white), ferric ferrocyanide, ferric ammonium ferrocyanide, and mixtures thereof.

The organic pigments include natural colorants and synthetic monomeric and polymeric colorants. Exemplary are aromatic compounds such as azo, triphenylmethane, indigo, anthraquinone, and xanthine dyes, which are referred to as D&C or FD&C pigments. Also useful are lakes, which are pigments formed by the precipitation and absorption of organic dyes in an insoluble base, such as alumina, barium, or calcium hydrates. Particularly preferred lakes are primary FD&C or D&C Lakes and blends thereof. Pigment concentrations will vary depending upon the color of the final product, but generally will be in the range of from about 0.1 to about 30 percent by weight of the total composition.

The composition can also contain small amounts of fillers or powders. Examples of such silica, talc, mica, starch, nylon, kaolin, bismuth oxychloride, or coated versions of each of these, for example, with lecithin, silicones, amino acids, fatty acids, fatty alcohols, or metallic soap coatings.

Further, the composition can contain other optional components including, but not limited to, oil soluble sunscreens, such as octyl methoxycinnamate; particulate sunscreens such as zinc oxide; oil-soluble antioxidants and/or preservatives, such as butylated hydroxytoluene ("BHT"); chelating agents such as disodium ethylene diamine tetra acetic acid ("EDTA"); fragrances (such as pinene); flavoring agents; waterproofing agents (such as PVP/eicosene copolymer); surfactants, such as silicone copolyols or fatty acid glycerol esters; and oil-soluble actives, such as tocopherol and its derivatives or retinol and its derivatives; and the like.

In one preferred embodiment, the compositions of the present invention are in the form of a foundation. The foundation is a light and creamy substance similar to that of a somewhat dry chocolate mousse or a hair mousse. As the foundation is applied to the skin and it is gently agitated (e.g., by means of rubbing), the texture of the foundations changes. It becomes powdery to the touch and feels light, soft and powdery on the skin. Particularly preferred are cosmetic compositions comprising trimethylsiloxysiloxate as the film forming agent for the hydrocarbon oil cosmetically acceptable carrier.

In another preferred embodiment, the compositions are in the form of a lip paint. The lip paint is easily applied and has a viscosity such that it can be applied to the lip without running. Similar to the foundation, as it is applied to the lip, the texture of the lip paint transforms and feels soft and velvety on the lips.

The invention is further illustrated by the following non-limiting example.

EXAMPLE

I. Makeup Formulation

| Material | Weight % |
| --- | --- |
| Cyclomethicone/trimethylsiloxysilicate | 3.0 |
| Isododecane | 4.0 |
| Silicone Gel | 55.0 |
| (50:50 organopolysiloxane elastomer in isododecane) | |
| Nylon-12 | 16.0 |
| Barium Sulfate | 2.0 |
| Mica | 5.9 |
| Dyes and pigments | 12.6 |
| Aluminum starch octenylsuccinate | 1.5 |

The constituents of the above formula are mixed thoroughly together. Any standard homogenizing or mixing apparatus known in the art can be used to carry out the mixing operation.

II. Measurement of Unique Soft Powdery Feel

A makeup foundation according to the present invention, containing a silicone gel combined with a compatible cosmetically acceptable carrier is tested using a panel of 20 female individuals. Qualifying panelists are selected from ages 18 to 55. They have normal, normal-oily, or oily facial skin, have a light to medium skin tone, and are regular users of a liquid foundation at least 5 days a week. Chosen panelists participate in an unidentified one day monadic study and complete a questionnaire at the close of the study. The questionnaire allows the panelists to rate various properties of the composition of the present invention. The panelists respond to questions about the properties of the composition using a five point scale (e.g. ranging from excellent/very good to poor).

Various portions of the questionnaire correspond to different characteristics of the composition. For example, a Performance Rating portion of the questionnaire examines the ability of the composition to maintain its appearance on the skin throughout the day, the texture of the composition, whether the composition feels greasy or oily on the skin, whether the composition is transfer-resistant, and whether the composition is long wearing (i.e. whether the composition lasts over a long period of time). The scale for this portion ranges from excellent to poor.

Another portion of the questionnaire, a Texture Rating, examines in more detail the texture of the composition. The panelists rate how smooth or soft, lightweight, powdery, or greasy or oily the composition is. The five point scale for this portion is divided into categories of extremely, very, somewhat, slightly and not at all. Further, an Application Rating portion of the questionnaire, allows the panelists to rate the slip and drag of the composition as it is applied to the skin. This rating portion is divided into a five point scale ranging from much too much slip, somewhat too much slip, just right - neither slips or drags, somewhat too much drag, to much too much drag. Further still, a Finish Rating examines whether the composition has a finish that is matte or shiny. The five point scale for this rating is very matte, somewhat matte, neither matte or shiny, somewhat shiny, and very shiny.

The results of the questionnaire for the Performance Rating indicate that 14 out of 20 panelists rate the composition excellent/very good for product texture, feeling lightweight on the skin, not feeling greasy/oily, being transfer-resistant and being long wearing, and that 15 out of 20 rate the composition as excellent/very good for maintaining appearance throughout the day. In the Texture Rating portion of the questionnaire, 18 out of 20 panelists find that the composition is extremely/very smooth or soft; 15 out of 20 panelists find the composition to be extremely/very lightweight; and 11 out of 20 panelists rate the composition extremely/very powdery. In addition, the Application Rating portion reveals that the composition, according to 15 out of 20 panelists, is just right—neither slips nor drags. Finally, 18 out of 20 of the panelists find the composition to be very or somewhat matte.

The soft powdery feel conferred by the composition of the invention is evaluated by comparing the present invention with a current brand of foundation used by the panelists which is otherwise a comparable makeup formulation. A portion of the questionnaire is entitled Compared to Brand Used Most Often and has a five point scale divided into sections of liked much more, somewhat more, same as, somewhat less, and much less. The results show the makeup composition of the present invention is liked much more or somewhat more by 14 out of 20 panelists for not feeling greasy or oily and for its texture.

III. Lip Paint Formulation

| Material | Weight % |
| --- | --- |
| Silicone Gel | 30 |
| (50:50 organopolysiloxane elastomer in isododecane) | |
| Cyclomethicone/trimethylsiloxysilicate | 22 |
| Mica | 12 |
| Isododecane | 12 |
| Dyes and pigments | 6 |
| Sorbitan Sesquioleate | 2.8 |
| Fragrance | 0.2 |

The constituents of the above formula are mixed thoroughly together. Any standard homogenizing or mixing apparatus known to the art can be used to carry out the mixing operation.

What we claim is:

1. A cosmetic composition for topical application to the skin containing about 30 to 60 percent by weight of the composition of a silicone gel comprising an organopolysiloxane elastomer pre-dispersed in a hydrocarbon vehicle, in combination with a cosmetically acceptable carrier comprising a volatile branched hydrocarbon oil, wherein said elastomer is a reaction product of an organopolysiloxane having an unsaturated group bonded to at least one terminal silicon atom and a silicone compound, said reaction product is at least partially cross-linked.

2. The composition of claim 1 wherein said silicone gel is present in an amount of about 5 to about 60 percent by weight.

3. The composition of claim 1 wherein said carrier is present in an amount of about 0.5 to about 60 percent by weight.

4. The composition of claim 3 wherein said carrier is a branched hydrocarbon oil having 1 to 14 carbon atoms.

5. The composition of claim 4 wherein said carrier is isodecane.

6. The composition of claim 1 wherein said hydrocarbon vehicle is present in an amount of about at least about 5 to about 60 percent by weight.

7. The composition of claim 6 wherein said vehicle is a linear or branched hydrocarbon oil having 1 to 14 carbon atoms.

8. The composition of claim 7 wherein said hydrocarbon oil is isododecane.

9. The composition of claim 1 which further comprises one or more pigments.

10. The composition of claim 1 which further comprises a film forming agent in an amount of from about 0.1 to about 20 percent by weight.

11. The composition of claim 10 wherein said film forming agent is trimethylsiloxysilicate.

12. The composition of claim 1 which is an anhydrous composition.

13. The composition of claim 12 wherein said composition is a lip product.

14. The composition of claim 12 wherein said composition is a foundation.

15. A method of producing a composition having a powdery sensation on the skin comprising adding to a compatible cosmetically acceptable carrier comprising about 30 to 60 percent by weight of the composition of a volatile branched hydrocarbon oil, a silicone gel comprising an organopolysiloxane elastomer pre-dispersed in a hydrocarbon vehicle, wherein said elastomer is a reaction product of an organopolysiloxane having an unsaturated group bonded to at least one terminal silicon atom and a silicone compound, said reaction product is at least partially cross-linked.

* * * * *